(12) United States Patent
Mazzuca et al.

(10) Patent No.: US 8,147,528 B2
(45) Date of Patent: Apr. 3, 2012

(54) LAMINOPLASTY METHODS AND DEVICES

(75) Inventors: Michael Mazzuca, North Easton, MA (US); Michael Jacene, Blackstone, MA (US); Ed Zalenski, Lakeville, MA (US); John Riley Hawkins, Cumberland, RI (US); Michael A. Fisher, Middleborough, MA (US)

(73) Assignee: DePuy Spine, Inc., Raynham, MA (US)

( * ) Notice: Subject to any disclaimer, the term of this patent is extended or adjusted under 35 U.S.C. 154(b) by 310 days.

(21) Appl. No.: 12/406,749

(22) Filed: Mar. 18, 2009

(65) Prior Publication Data
US 2010/0241230 A1    Sep. 23, 2010

(51) Int. Cl.
*A61B 17/66* (2006.01)

(52) U.S. Cl. ....... 606/282; 606/280; 606/90; 623/17.11; 623/17.16

(58) Field of Classification Search .......... 606/246–279, 606/300–321, 324, 90, 280, 282; 623/17.11–17.16
See application file for complete search history.

(56) References Cited

U.S. PATENT DOCUMENTS

| | | | |
|---|---|---|---|
| 2,580,821 A | 1/1952 | Toufick | |
| 5,176,679 A | 1/1993 | Lin | |
| 6,080,157 A | 6/2000 | Cathro et al. | |
| 6,358,254 B1 | 3/2002 | Anderson | |
| 6,712,852 B1 | 3/2004 | Chung et al. | |
| 7,166,107 B2 | 1/2007 | Anderson | |
| 7,264,620 B2 | 9/2007 | Taylor | |
| 2004/0030388 A1 | 2/2004 | Null et al. | |
| 2004/0064140 A1* | 4/2004 | Taylor et al. | 606/61 |
| 2004/0107003 A1 | 6/2004 | Boyer et al. | |
| 2005/0119657 A1 | 6/2005 | Goldsmith | |
| 2005/0171539 A1 | 8/2005 | Braun et al. | |
| 2006/0036259 A1* | 2/2006 | Carl et al. | 606/90 |
| 2006/0084985 A1 | 4/2006 | Kim | |
| 2007/0049937 A1 | 3/2007 | Matthis et al. | |
| 2007/0055236 A1 | 3/2007 | Hudgins et al. | |
| 2007/0073405 A1 | 3/2007 | Verhulst et al. | |
| 2007/0191837 A1 | 8/2007 | Trieu | |
| 2007/0219634 A1 | 9/2007 | Greenhalgh et al. | |
| 2008/0009865 A1* | 1/2008 | Taylor | 606/61 |
| 2009/0210012 A1 | 8/2009 | Null et al. | |
| 2010/0241165 A1 | 9/2010 | Konieczynski et al. | |

FOREIGN PATENT DOCUMENTS

WO    03101319 A2    12/2003

OTHER PUBLICATIONS

Intl. Search Report PCT/US2010/024698, Apr. 23, 2010.
Intl. Search Report PCT/US2010/024705, Apr. 23, 2010.

* cited by examiner

*Primary Examiner* — Eduardo C Robert
*Assistant Examiner* — Christina Negrelli
(74) *Attorney, Agent, or Firm* — Nutter McClennen & Fish LLP

(57) ABSTRACT

A vertebral implant is provided that includes a distraction member having a first end configured to pivotally couple to a first cut portion of a vertebra and a second end configured to mate with a base member configured to couple to a second cut portion of the vertebra. The distraction member can move relative to the base member to create a force effective to adjust a distance between the first and second cut portions of the vertebra.

23 Claims, 6 Drawing Sheets

LAMINOPLASTY METHODS AND DEVICES

FIELD OF THE INVENTION

The present invention relates to methods and devices for increasing the size of a spinal canal.

BACKGROUND OF THE INVENTION

In certain pathologies, the spinal canal extending through a patient's vertebrae is or becomes too narrow and constricts the spinal cord extending therethrough. The narrowing may be congenital, potentially affecting patients at any age. Narrowing can also be attributable to other causes, such as age, injury or removal of a spinal disk.

A condition associated with aging, for instance, is spondylosis, in which intervertebral disc loose water and become less dense. These degenerative changes near the disk can cause an overgrowth of the bone, producing bony spurs called "osteophytes" that can compress the spinal cord. The constriction of the spinal cord in the cervical spine, for example, often produces pain, weakness, or loss of feeling in extremities. Other causes for narrowing of the spinal canal include disc shrinkage, which causes the disc space to narrow and the annulus to bulge and mushroom out, resulting in pressure on the spinal cord. Degenerative arthritis of facet joints can cause joints to enlarge, or the vertebra to slip with respect to each other, also compressing the spinal cord. Instability between vertebra, such as caused by stretched and thickened ligaments' can also produce pressure on the spinal cord and nerve roots.

Myelopathy, or malfunction of the spinal cord, occurs due to its compression. The rubbing of the spine against the cord can also contribute to this condition, and the spinal cord compression can ultimately compromise the blood vessels feeding the spinal core, further aggravating the myelopathy.

Traditional procedures for decompressing the spinal cord include a laminectomy, in which the lamina and spinal processes are removed to expose the dura covering the spinal cord. Another known procedure is a laminoplasty, in which the lamina is lifted off the dura, but not completely removed. Typically, one side of the lamina is cut, while a partial cut is made on the other side to hinge the lamina away from the spinal cord to increase the size of the spinal canal. A laminoplasty plate is then screwed to a lateral mass and to the hinged open lamina. A strut of bone can be placed in the open portion within the lamina and the lateral mass to help hold the open position of the lamina. Prior to the operation, the surgeon needs to measure the vertebra to determine the size of the plate necessary for implantation. At that point, a plate can be selected with the appropriate dimensions, and implanted at the site. There can be difficulty in the determination of the appropriate plate as the measurements must have sufficient accuracy as to make the correct plate selection.

Accordingly, there is a need for improved methods and devices for increasing the size of the spinal canal.

SUMMARY OF THE INVENTION

The present invention provides various devices and methods for increasing the size of a spinal canal. In one embodiment, a vertebral implant is provided and includes a distraction member having a first end configured to pivotally couple to a first cut portion of a vertebra and a second end configured to mate with an opening formed in a base member configured to couple to a second cut portion of the vertebra. The distraction member can move through the opening to create a force effective to adjust a distance between the first and second cut portions of the vertebra. For example, the distraction member can be threadably mated to the opening in the base member. In one embodiment, the distraction member can include an anchor pivotally coupled thereto for pivotally anchoring the distraction member to the first cut portion of the vertebra. The anchor and the distraction member can be mated, for example, by a ball and socket joint. The base member can include a fastener adapted to couple the base member to the second cut portion of the vertebra, and the fastener can be disposed through a bore in the base member. The base member can optionally include a clamp configured to fit around the second cut portion of the vertebra.

The implant can also include various features to fix the position of the threaded member relative to the base member. In one embodiment, the implant can include a locking mechanism coupled to the distraction member and configured to lock the distraction member in a fixed position relative to the base member. In another embodiment, the second end of the distraction member can have a size that is greater than a size of the opening formed in the base member to prevent the second end of the distraction member from passing through the opening in the base member.

In another embodiment, a vertebral implant is provided and includes a base member having a first portion configured to couple to a first cut portion of a vertebra and a second portion with a threaded bore formed therethrough. The implant can also include a threaded member configured to pivotally couple to a second cut portion of a vertebra and threadably disposed through the threaded bore such that rotation of the threaded member relative to the base member is effective to adjust a distance between the first and second cut portions of the vertebra. In one exemplary embodiment, the threaded member can include an anchor pivotally coupled thereto for anchoring the threaded member to the second cut portion such that the threaded member is pivotally movable relative to the second cut portion of the vertebra. The anchor and the threaded member can be mated, for example, by a ball and socket joint. The threaded bore can be a first bore and the base member can include a second bore for receiving a fastener for coupling to the first cut portion of the vertebra. The first portion of the base member can also include a clamp configured to fit around the second cut portion of the vertebra to secure the base member to the second cut portion of the vertebra. In another embodiment, the threaded member can be cannulated.

The implant can also include various features to fix the position of the threaded member relative to the base member. In one exemplary embodiment, the implant can include a locking mechanism coupled to the threaded member and configured to lock the threaded member in a fixed position relative to the base member. In another embodiment, the threaded member can have a first end configured to couple to the second cut portion of the vertebra and a second end extending through the threaded bore. The second end of the threaded member can have a size that is greater than a size of the threaded bore formed in the base member to prevent the second end of the threaded member from passing through the threaded bore.

Methods for increasing a size of a spinal canal are also provided, and in one embodiment the method can include pivotally coupling a distraction member to a first cut portion of a vertebra, coupling a base member to a second cut portion the vertebra, and actuating the distraction member to apply a force to the base member to adjust a distance between the first and second cut portions of the vertebrae. The distraction member can be threadably rotated through a threaded opening formed in the base member to adjust the distance between the first and second cut portions. In one exemplary embodiment, the method can include locking a locking mechanism coupled to the distraction member to prevent movement of the distraction member relative to the base member. In another exemplary embodiment, the method can include cutting through the lamina of the vertebra to form the first and second cut portions, for example, after coupling at least one of the distraction member and the base member to the vertebra. Pivotally coupling the distraction member to the first cut portion of the vertebra can include coupling an anchor pivotally mated to the distraction member to the first cut portion of the vertebra. Coupling the base member to the second cut portion of vertebra can include inserting a fastener through an opening formed in the base member and into the second cut portion of the vertebra.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various methods and device for increasing the size of a spinal canal. In general, a vertebral implant is provided that is adapted to couple cut portions of a vertebra to increase a distance between the cut portions in order to increase the size of the spinal canal of the vertebra. In an exemplary embodiment, the vertebral implants disclosed herein allow for in-situ adjustment of the distance between the cut portions, thereby eliminating the need to measure the space and/or select an implant having an appropriate size. The implants can also be configured to have a variable trajectory such that the implant can adjust accordingly during expansion of the space between the cut portions of bone.

Figure 1:
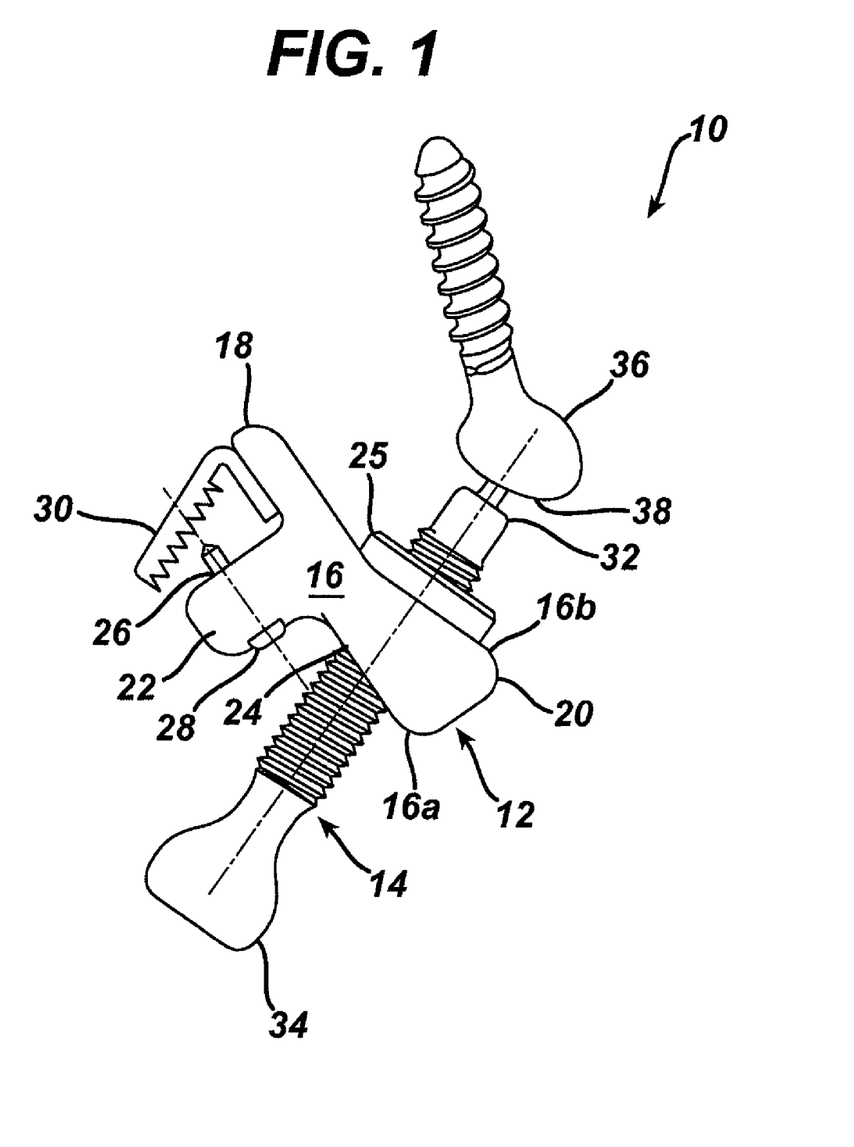
FIG. 1 is a perspective view of a vertebral implant having a base member and a distraction member for increasing the size of a spinal canal of a vertebra.
Figure 2A:
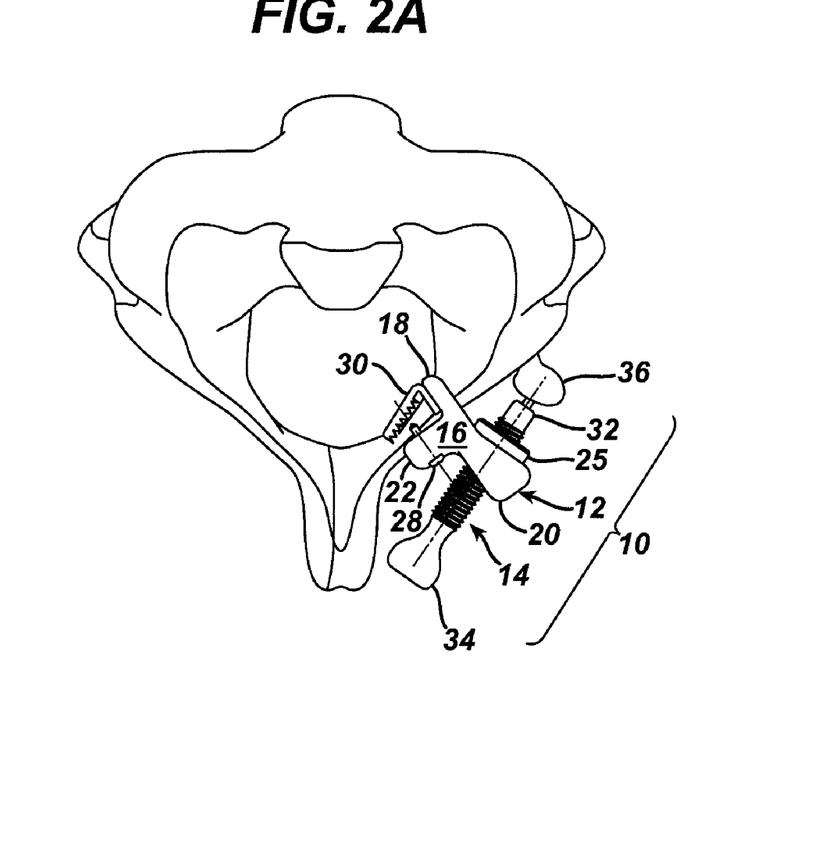
FIG. 2A is a top view of a vertebra having the vertebral implant of FIG. 1 coupled to opposed sides of a cut in the vertebra.
Figure 2B:
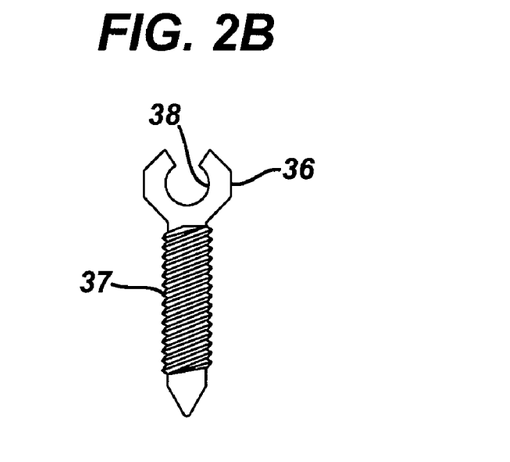
FIG. 2B is a cross-sectional view of an anchor for use with the vertebral implant of FIG. 2A.
Figure 3:
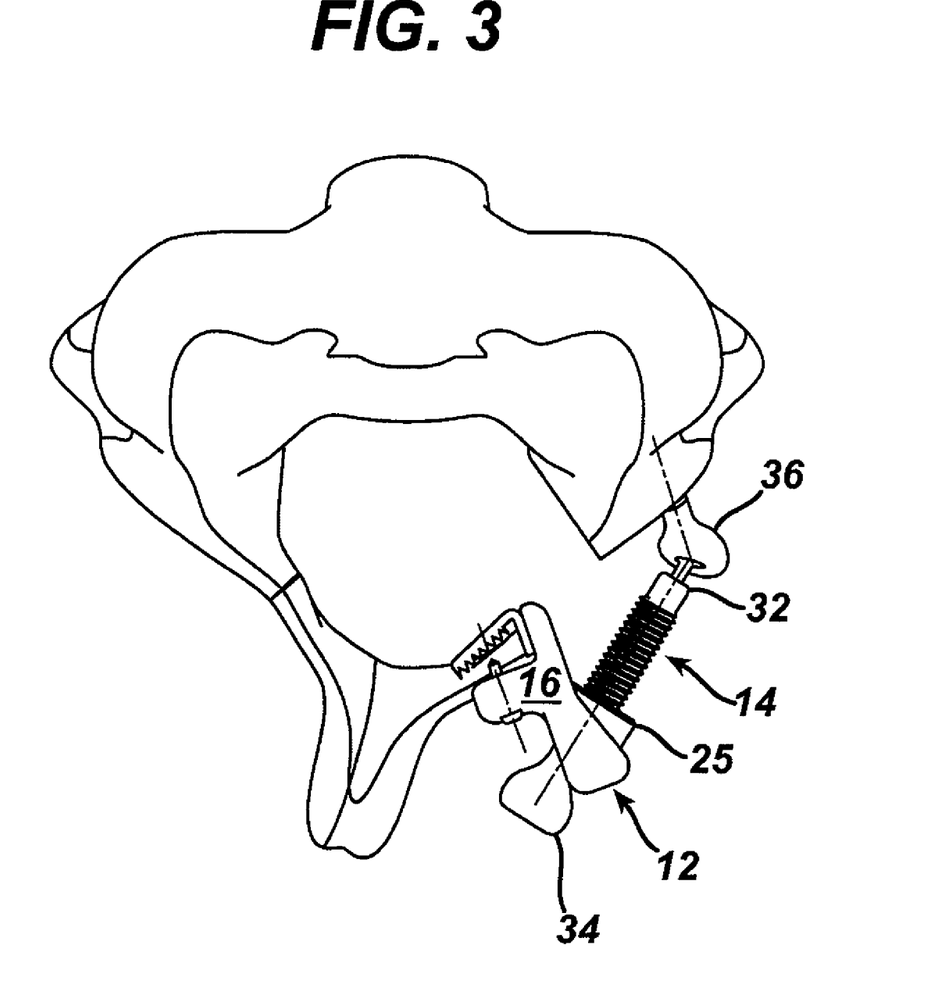
FIG. 3 is a top view of the vertebra and vertebral implant of FIG. 2A showing the implant expanded to increase the size of a spinal canal of the vertebra.

FIGS. 1-3 illustrate one exemplary embodiment of a vertebral implant 10 that generally includes a base member 12 configured to couple to a first cut portion of a vertebra and a distraction member 14 configured to couple to a second cut portion of the vertebra. The distraction member 14 can be coupled to the base member 12 such that the distraction member 14 is configured to apply a force to the base member 12 that is effective to increase a distance between the first and second cut portions, and thus increase the size of a spinal canal of the vertebra.

The base member 12 can have a variety of configurations. In the embodiment illustrated in FIGS. 1-3, the base member 12 has an elongate plate-like portion 16 with first and second opposed surfaces 16a, 16b extending between first and second opposed ends 18, 20. The surfaces 16a, 16b can be planar, or they can have a shape to facilitate insertion between two cut portions of bone. As shown in FIG. 1, the surfaces 16a, 16b are parallel to one another from the first end 18 toward or to a substantial mid-region, where the surfaces 16a, 16b taper away from one another toward the second end 20. As further shown in FIGS. 1 and 2A, a projection 22 can extend outward from the first surface 16a at a location between the first and second ends 18, 20 and a bore 24 can extend through the first and second surfaces 16a, 16b at a location between the bore 24 and the second end 20 for receiving the distraction member 14. The projection 22 can also have a plate-like configuration such that the elongate portion 16 and the projection 22 form a T-shaped base. As a result, the projection 22 can extend along the outside of a vertebra and the first end 18 of the elongate portion 16 can extend into a cut formed in the vertebra. The projection 22 can also include a bore 26 extending therethrough and configured to receive a fastener to couple the base member 12 to bone. The fastener can have a variety of configurations, but in the illustrated embodiment it is in the form a screw 28 configured to be inserted into the bore 26 and into bone. The base member 12 can also optionally include a clamp 30 formed thereon or coupled thereto that extends from the first end 18 of the elongate portion 16 of the base member 12 and that extends substantially parallel to the projection 22 so that the clamp 30 and the projection 22 can engage bone therebetween, as shown in FIG. 2A. The clamp 30 can have various configurations, but in the illustrated embodiment it is L-shaped to allow one end to rest along and be mated to the first surface 16a of the elongate portion 16, and to allow the other end to extend substantially parallel to or at a slight angle relative to the projection 22. The clamp 30 can also include surface features, such as teeth, for engaging bone. A person skilled in the art will appreciate that, while the illustrated clamp 30 is shown attached to the base member 12, the clamp 30 can be integrally formed with the base member 12.

The base member 12 can be formed from a variety of materials, but in an exemplary embodiment the base member is preferably substantially rigid to facilitate rigid mating to the second cut portion of the vertebra. The clamp 30 can also be rigid, or it can be slightly flexible to allow the clamp 30 to be compressed into bone. A person skilled in the art will appreciate that the base member 12 can have any configuration that facilitates coupling to the second cut portion of the vertebra and to the distraction member 14.

The second end 20 of the elongate portion 16 of the base member 12 can be configured to couple to the distraction member 14 to allow the distraction member 14 to move relative to the base member 12 to increase a distance between first and second cut portions of the vertebra. While the movement between the base member 12 and the distraction member 14 can be achieved in a variety of ways, in the illustrated embodiment the bore 24 in the second end 20 of the elongate portion 16 of the base member 12 is threaded and the distraction member 14 is threaded to threadably engage the bore 24. The threads of the bore 24 correspond to the threads of the distraction member 14 to allow the distraction member 14 to rotate relative to the bore 24 to increase the distance between first and second cut portions of the vertebra coupled to the base member 12 and the distraction member 14. While the bore 24 itself can be threaded, in an exemplary embodiment as shown the threads are formed in a threaded bushing 25 that is movably seated within the bore 24. The bushing 25 can include an exterior surface sized to permit pivotal and/or rotational movement of the bushing 25 within the bore 24 of the base member 12, thus allowing the trajectory of the distraction member 14 relative to the base member 12 to vary. For example, the bushing 25 can have a partially spherical or convex outer surface and the bore 24 can have a spherical or concave inner surface to allow pivotal and angular movement of the bushing 25 within the bore 24. The bore 24 can be sized and shaped to prevent the bushing 25 from passing therethrough, for example, to prevent the bushing 25 from passing through the bore 24 during distraction as the distance between the first and second cut portions is being increased.

The distraction member 14 can also have a variety of configurations. In the embodiment illustrated in FIGS. 1-3, the distraction member 14 is generally in the form of a threaded elongate shaft having a first end 32 configured to couple to the first cut portion of the vertebra and a second end 34 with a head formed thereon for driving the distraction member 14 relative to the base member 12. While the length of the distraction member 14 can vary, the distraction member 14 preferably has a length that is sufficient to increase a distance between the first and second cut portions of the vertebra so as to increase the size of the spinal canal as needed. The distraction member 14 can be threaded substantially along its entire length, or it can be threaded on a portion of its length depending on the desired increase in distance between the first and second cut portions of the vertebra. In the illustrated embodiment, the distraction member 14 is threaded along substantially the entire length thereof to maximize variation in distance between the first and second cut portions as the distraction member 14 moves relative to the base member 12.

The head on the second end 34 of the distraction member 14 can have various configurations, but it is preferably adapted to prevent the second end 34 of the distraction member 14 from passing through the bore 24 of the base member 12 and separating from the base member 12. In one exemplary embodiment, the head can have a size that is greater than the size of the bore 24 formed in the base member 12. The larger size of the head of the distraction member 14 prevents the second end 34 from passing through the bore 24 and separating from the base member 12. While not shown, the head can also include a drive feature, such as a slot or shaped outer surface (e.g., hexagonal), to allow a driver tool to engage and rotate the distraction member 14 relative to the base member 12.

The first end 32 of the distraction member 14 can be coupled to bone in a variety of ways. In one exemplary embodiment as shown, the first end 32 of the distraction member 14 is mated to an anchor 36 for anchoring the distraction member 14 to bone. While the mating technique can vary, in one embodiment the distraction member 14 and the anchor 36 are pivotally mated to allow the angular orientation of the distraction member 14 relative to the bone to change as the distraction member 14 is rotated to separate the cut portions of bone. In order to allow such pivotal movement, in one embodiment the anchor 36 can include a distal threaded shank configured to extend into and engage the bone and a proximal head having a socket 38, shown in FIG. 2B, configured to receive the first end of the distraction member 14. The first end 32 of the distraction member 14 can include a spherical or partially spherical member or ball formed on a terminal end thereof that is adapted to be rotatably and pivotally disposed within the socket 38 formed in the anchor 36 to form a ball and socket joint. In particular, the anchor 36 can include a concave recess therein to form the socket 38. When the ball formed on the first end 32 of the distraction member 14 is disposed within the socket 38 of the anchor 36, the ball will be movably captured within the socket 38 to allow pivotal movement of the first end 32 of the distraction member 14 relative to the anchor 36, thus allowing movement of the distraction member 14 relative to the base member 12. A person skilled in the art will appreciate that the first end 32 of the distraction member 14 can couple to the first cut portion of the vertebra using a variety of configurations, including any other configuration that does or does not allow the first end 32 to move relative to the bone.

In another embodiment, the first end 32 of the threaded member 14 can be configured to non-pivotally couple to the first cut portion, as illustrated in FIGS. 4-8. In one embodiment shown in FIGS. 4-5, the distraction member 114 is formed from a first threaded element 132 and a second threaded element 134. The first threaded element 132 includes a threaded shank configured to be threaded into bone and having a distal tip configured to penetrate bone. The second threaded element 134 is in the form of an elongate shaft having external threads formed along the length thereof for threadably engaging a bore in a base member 112, and having a bore extending into at least a distal end thereof for receiving a proximal end of the first threaded element 132. The base member 112 can have a variety of configurations, but in the illustrated embodiment it is in the form of a rectangular member 115 having an elongate projection 117 extending therefrom to form an L-shaped base. The rectangular member 115 can include the bore extending therethrough for engaging the distraction member 114. The rectangular member 115 can extend along the outside of the vertebra and the projection 117 can extend between the cut portions of the vertebra. As further shown in FIGS. 4-5, the projection 117 can also include a curved tip or other features formed thereon or attached thereto to engage the cut portion of bone.

Figure 4:
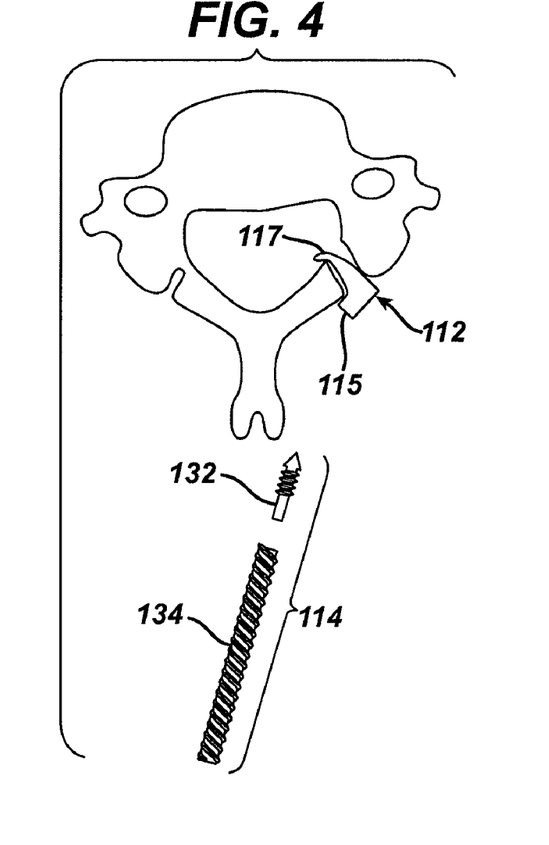
FIG. 4 is a top view of a vertebra having another embodiment of a vertebral implant positioned in a cut formed in the vertebra.
Figure 5:
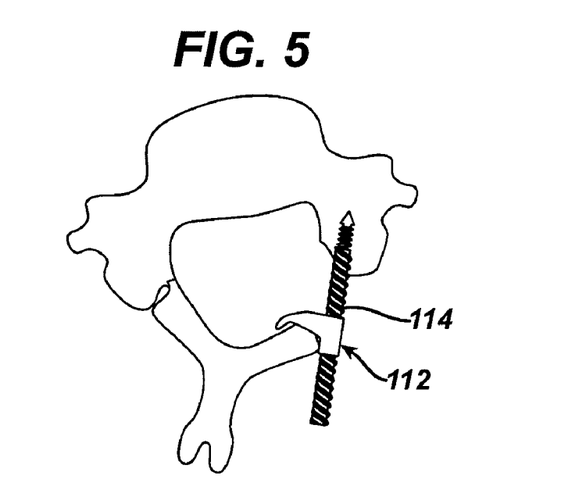
FIG. 5 is a top view of the vertebra and vertebral implant of FIG. 4 with the size of a spinal canal of the vertebra increased.

The first element 132 and the second element 134 of the distraction member 114 can be coupled together in a variety of ways. In one exemplary embodiment (not shown), the first element 132 can include a concave recess formed in its distal end to form a socket, and the second element 134 can include a ball formed on its proximal end that is disposed within the socket to allow pivotal movement between the first and second elements 132, 134. The ball and socket can include corresponding features formed thereon to allow the ball to snap into the socket. In another exemplary embodiment, the proximal end of the first element 132 can be inserted into a recess formed in the distal end of the second element 134 such that the first and second elements 132, 134 are held together by an interference fit. A person skilled in the art will appreciate that the first and second elements 132, 134 can be coupled together using any technique known in the art. The proximal end of the first element 132 can also be merely received within the distal end of the second element 134 without any mating features.

Figure 6:
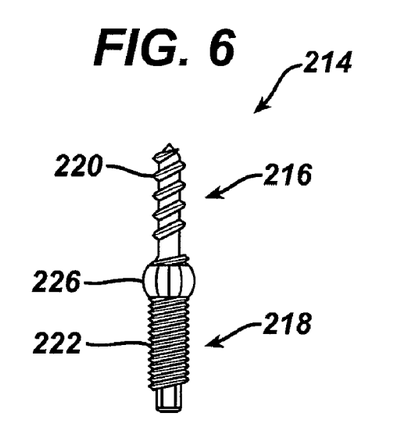
FIG. 6 is a side view of another embodiment of a distraction member of a vertebral implant for increasing the size of a spinal canal of a vertebra having first and second threaded portions.
Figure 7A:
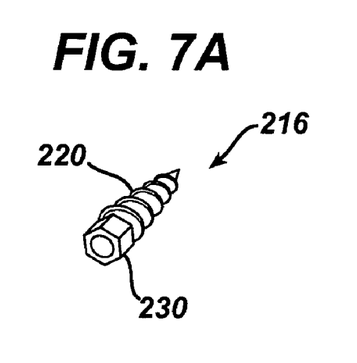
FIG. 7A is a perspective view of the first threaded portion of the distraction member of FIG. 6.
Figure 7B:
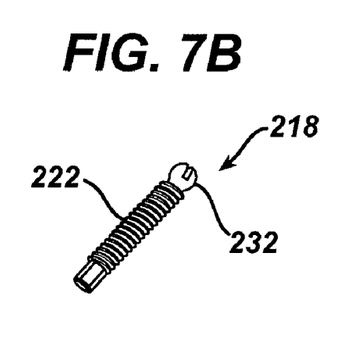
FIG. 7B is a perspective view of the second threaded portion of the distraction member of FIG. 6.
Figure 8:
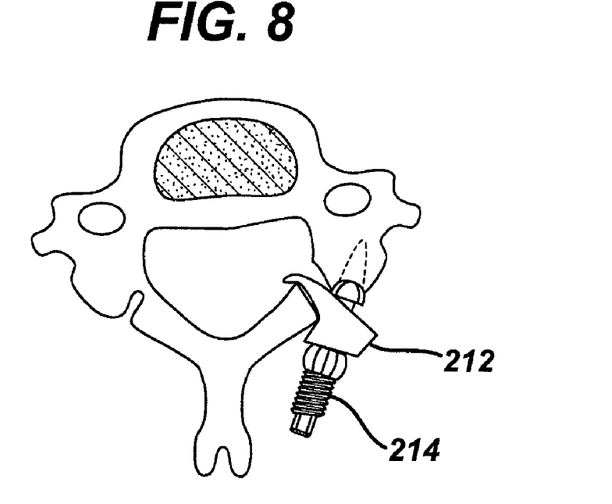
FIG. 8 is a top view of a vertebra having the vertebral implant of FIG. 6 coupled thereto for increasing the size of the spinal canal of the vertebra.

In another embodiment shown in FIGS. 6-8, the distraction member 214 can be formed from a first threaded element 216 and a second threaded element 218. The first threaded element 220 includes threads 220 formed along a distal portion thereof that are configured to mate to the first cut portion of the vertebra, for example, by being threaded into bone. The second threaded element 218 includes a threaded portion 222 having threads formed along substantially the entire length thereof to mate with threads formed in the base member 212, e.g., in a bushing 226 that is coupled to the base member 212 and that is configured to rotate relative to the second threaded element 218 to increase a distance between the first and second cut portions of the vertebra. The bushing 226 can have a rounded outer surface such that the bushing 226 can pivot relative to the base member 212 when the bushing 226 is seated within the bore of the base member 212. A person skilled in the art will appreciate that various other components can be used in place of the bushing 226 to allow the second threaded element 218 to rotate relative to the base member 212 to increase the distance between the first and second cut portions of the vertebra.

The first and second threaded elements 220, 222 of the distraction member 214 can be coupled together in a variety of ways. In the illustrated embodiment shown in FIGS. 7A-7B, a concave recess is formed in a proximal end of the first threaded element 216 to form a socket 230, and the second threaded element 218 includes a ball 232 formed on a distal end thereof that sits within the socket 230 of the first threaded element 216 to allow pivotal movement between the first and second elements 216, 218. In order to secure the ball 232 to the socket 230, the ball 232 and the socket 230 can include features formed thereon to snap the ball 232 inside the concave recess that forms the socket 230. For example, the ball 232 can include a slot formed therein, shown in FIG. 7B, that allows the ball 232 to deform upon insertion into the socket 230, and to expand once seated into the socket 230 to engage the socket 230 by snap-fit. A person skilled in the art will appreciate that the ball 232 and socket 230 need not securely mate, and that the ball 232 can be disposed within the socket 230 without any mating connection.

Figure 9:
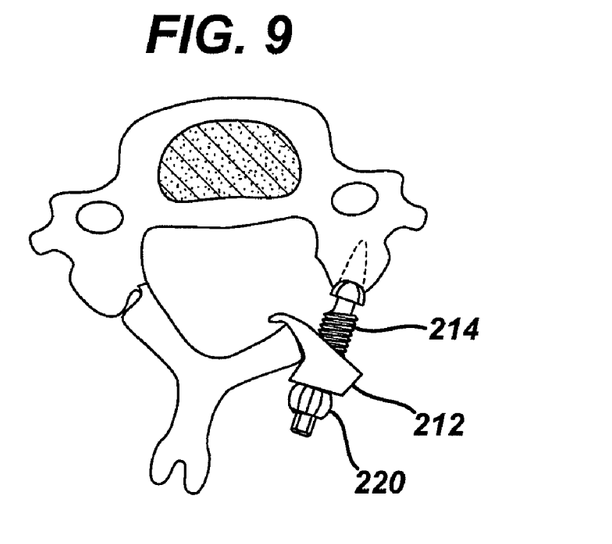
FIG. 9 is a top view of a vertebra having a vertebral implant coupled thereto having a base member and a distraction member, the implant including a locking mechanism configured to lock the distraction member relative to the base member.

In another embodiment shown in FIG. 9, the distraction member can include a locking mechanism configured to lock the distraction member in a fixed position relative to the base member. For example, a locking nut 220 having a threaded bore formed therein can be threadably disposed on the threaded portion of the distraction member. When the cut portion of bone is expanded to a desired distance, the nut 220 can be threaded toward and into contact with the bushing or base member 212 to lock the distraction member 214 relative to the base member 212. A person skilled in art will appreciate that the nut 220 can be used with any of the embodiments of the vertebral implants described herein. In yet another embodiment, the bushing disposed in the base member can include a crimp feature formed thereon that can be crimped to engage the distraction member and lock it relative to the base member. A person skilled in the art will appreciate that any technique can be used to lock the distraction member in a fixed position relative to the base member if desired.

Referring back to the embodiment of FIGS. 1-3, for example, the anchor 36 can also include features to facilitate implantation of the anchor 36 in bone with the distraction member 14 mated thereto. In one embodiment, an outer surface of the anchor 36 can have a shape that corresponds to the shape of an implantation portion of a tool. For example, the anchor 36 can have an outer surface that has a hexagonal shape, shown in FIG. 2B. The anchor 36 can be mated to the first cut portion using a tool that has a hexagonal drive socket that corresponds to the hexagonal shape of the outer surface of the anchor 36 such that the threaded portion 37 of the anchor 36 can be implanted into the vertebra by placing the inner surface of the tool over the distraction member 14 and over the outer surface of the anchor 36 and rotating the tool. A person skilled in the art will appreciate, however, that the outer surface of the anchor 36 can have any shape or configuration to facilitate engagement by a drive tool. For example, in another exemplary embodiment, the distraction member 14 can be cannulated such that a portion of an implantation tool can be inserted therethrough. The tool can be inserted through the distraction member 14 all the way along its length and through the ball formed on the end thereof and into the socket 38 in the anchor 36. Rotation of the tool is effective to rotate the anchor 36 and thread a threaded portion of the anchor 36 into the vertebra. In yet another exemplary embodiment, the bushing 25 of the base member 12 or the locking nut 220 can be used to lock the ball and socket 38 of the distraction member 14 and the anchor 36 together to prevent movement between the ball and socket 38 such that a tool can be used to engage the head on the distraction member 14 to drive the anchor 36 into bone. The bushing 25 can be rotated and advanced along the threads of the second end 34 of the distraction member 14 until the bushing 25 reaches the first end 32 of the distraction member 14 such that the bushing 25 fits around the ball and the socket 38 to lock them together.

Other exemplary embodiments of devices for increasing the size of a spinal canal are disclosed in U.S. patent application Ser. No. 12/406,726 filed on even date herewith and entitled "Laminoplasty Methods Using Hinge Device," which is hereby incorporated by reference in its entirety. A person skilled in the art will appreciate that any of the various embodiments disclosed in the aforementioned application can be used in any combination with the present invention.

The present invention also provides methods for increasing the size of the spinal canal. In one exemplary embodiment, the base member 12 and the distraction member 14 are coupled to the first and second cut portions of the vertebra. The cut between the first and second cut portions can be made to completely separate the first and second cut portions, and can be made on a portion of the vertebra, such as the lamina, before or after the base member 12 and/or the distraction member 14 are coupled thereto, but preferably the threaded portion of the anchor 36 of the distraction member 14 is mated to the first cut portion before the cut is made, and the base member 12 is mated to the second cut portion after the cut between the first and second cut portions is formed. Alternatively, the cut can be made between the first and second cut portions and then the base member 12 and the distraction member 14 can be coupled thereto. In one exemplary embodiment, a hinge can be formed in a lateral side of the vertebra opposite the first and second cut portions, for example, in the bone between the spinous process and the pedicles of the vertebra. The hinge can be advantageous when increasing the distance between the first and second cut portions of the vertebra. The base member 12 can be coupled to the first cut portion, for example, using one or more fasteners and/or the clamp 30 to engage bone of the first cut portion between the clamp 30 and the projection 22 of the base member 12. The distraction member 14 can be coupled to the second cut portion, for example, using the anchor 36 to pivotally mate the distraction member 14 to the second cut portion of the vertebra.

At the time of implantation of the vertebral implant 10, the base member 12 is located at an end of the distraction member 14 closer to the anchor 36 such that the first and second cut portions of the vertebra will be substantially adjacent to or in contact with one another. In order to increase the distance between the first and second cut portions, the second end 34 of the distraction member 14 is rotated, e.g., using a driving tool inserted into a drive socket in the head of the distraction member 14, through the threaded bore formed in the bushing 25 of the base member 12. Since the distal end of the distraction member 14 is fixed relative to the first cut portion of bone and this cannot move, rotation of the distraction member 14 applies force to the base member 12 to cause the base member 12 to move proximally along the distraction member 14 such that the base member 12 is forced away from the anchor 36. As the base member 12 moves away from the anchor 36 of the first end 32 of the distraction member 14, the distance between the anchor 36 and the base member 12 increases. This increases the distance between the first and second cut portions of the vertebra as the anchor 36 is coupled to the first cut portion and the base member 12 is coupled to the second cut portion. Thus, the first and second cut portions are forced apart. After the desired distance between the first and second cut portions of the vertebra is achieved, the relative positions of the base member 12 and distraction member 14 can optionally be locked in place using any of the techniques described above, including the use of the locking mechanism to lock the base member 12 relative to the distraction member 14, or crimping the bushing of the base member 12.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A vertebral implant, comprising:
   a base member having a plate with an opening formed therein and a clamp mated to the plate, the clamp being configured to fit around a first cut portion of a vertebra; and
   a distraction member having a first end configured to pivotally couple to a second cut portion of the vertebra and a second end configured to mate with the opening formed in the plate of the base member, wherein the distraction member can move through the opening to create a force effective to increase a distance between the first and second cut portions of the vertebra.

2. The implant of claim 1, wherein the distraction member includes an anchor pivotally coupled thereto for pivotally anchoring the distraction member to the second cut portion of the vertebra.

3. The implant of claim 2, wherein the anchor and the distraction member are mated by a ball and socket joint.

4. The implant of claim 1, wherein the base member includes a fastener adapted to couple the base member to the first cut portion of the vertebra.

5. The implant of claim 4, wherein the fastener is disposed through a bore in the base member.

6. The implant of claim 1, further comprising a locking mechanism coupled to the distraction member and configured to lock the distraction member in a fixed position relative to the base member.

7. The implant of claim 1, wherein the second end of the distraction member has a size that is greater than a size of the opening formed in the plate of the base member to prevent the second end of the distraction member from passing through the opening in the plate of the base member.

8. The implant of claim 1, wherein the distraction member is threadably mated to the opening in the plate of the base member.

9. A vertebral implant, comprising:
   a plate having a first end configured to couple to a first cut portion of a vertebra and a second end with a threaded bore formed therethrough; and
   a threaded member configured to pivotally couple to a second cut portion of a vertebra and threadably disposed through the threaded bore such that rotation of the threaded member relative to the plate is effective to increase a distance between the first and second cut portions of the vertebra.

10. The implant of claim 9, wherein the threaded member includes an anchor pivotally coupled thereto for anchoring the threaded member to the second cut portion such that the threaded member is pivotally movable relative to the second cut portion of the vertebra.

11. The implant of claim 10, wherein the anchor and the threaded member are mated by a ball and socket joint.

12. The implant of claim 9, wherein the threaded bore comprises a first bore and the plate includes a second bore for receiving a fastener for coupling to the first cut portion of the vertebra.

13. The implant of claim 9, further comprising a locking mechanism coupled to the threaded member and configured to lock the threaded member in a fixed position relative to the plate.

14. The implant of claim 9, wherein the threaded member has a first end configured to couple to the second cut portion of the vertebra and a second end extending through the threaded bore.

15. The implant of claim 14, wherein the second end of the threaded member has a size that is greater than a size of the threaded bore formed in the plate to prevent the second end of the threaded member from passing through the threaded bore.

16. The implant of claim 9, wherein the first portion of the plate comprises a clamp configured to fit around the second cut portion of the vertebra to secure the plate to the second cut portion of the vertebra.

17. The implant of claim 9, wherein the threaded member is cannulated.

18. A method for increasing a size of a spinal canal, comprising:
   pivotally coupling a distraction member to a first cut portion of a vertebra;
   coupling a base member to a second cut portion the vertebra; and
   actuating the distraction member to apply a force to the base member to adjust a distance between the first and second cut portions of the vertebrae;
   wherein adjusting the distance between the first and second cut portions comprising threadably rotating the distraction member through a threaded opening formed in the base member.

19. The method of claim 18, further comprising locking a locking mechanism coupled to the distraction member to prevent movement of the distraction member relative to the base member.

20. The method of claim 18, further comprising cutting through the lamina of the vertebra to form the first and second cut portions.

21. The method of claim 20, wherein cutting through the lamina occurs after coupling at least one of the distraction member and the base member to the vertebra.

22. The method of claim 18, wherein pivotally coupling the distraction member to the first cut portion of the vertebra comprises coupling an anchor pivotally mated to the distraction member to the first cut portion of the vertebra.

23. The method of claim 18, wherein coupling the base member to the second cut portion of vertebra comprises inserting a fastener through an opening formed in the base member and into the second cut portion of the vertebra.

* * * * *